(12) United States Patent
Steele

(10) Patent No.: US 10,456,161 B2
(45) Date of Patent: Oct. 29, 2019

(54) TISSUE-REMOVING CATHETER WITH ADJUSTMENT MECHANISM

(71) Applicant: Covidien LP, Mansfield, MA (US)

(72) Inventor: Bradley Steele, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 588 days.

(21) Appl. No.: 15/099,331

(22) Filed: Apr. 14, 2016

(65) Prior Publication Data

US 2017/0296222 A1 Oct. 19, 2017

(51) Int. Cl.
*A61B 17/3207* (2006.01)
*A61B 17/00* (2006.01)

(52) U.S. Cl.
CPC ........ *A61B 17/320783* (2013.01); *A61B 17/320725* (2013.01); *A61B 17/320758* (2013.01); *A61B 2017/003* (2013.01); *A61B 2017/00327* (2013.01); *A61B 2017/320791* (2013.01)

(58) Field of Classification Search
CPC .... A61B 17/320725; A61B 17/320758; A61B 17/320783; A61B 2017/003; A61B 2017/00327; A61B 17/3207; A61B 17/00
See application file for complete search history.

(56) References Cited

U.S. PATENT DOCUMENTS

| | | |
|---|---|---|
| 4,290,427 A | 9/1981 | Chin |
| 4,631,052 A | 12/1986 | Kensey |
| 4,765,332 A | 8/1988 | Fischell et al. |
| 4,790,813 A | 12/1988 | Kensey |
| 4,926,858 A | 5/1990 | Gifford, III et al. |
| 4,950,277 A | 8/1990 | Farr |
| 5,026,383 A | 6/1991 | Nobles |
| 5,085,662 A | 2/1992 | Willard |
| 5,100,424 A | 3/1992 | Jang et al. |
| 5,123,904 A | 6/1992 | Shimomura et al. |
| 5,176,693 A | 1/1993 | Pannek, Jr. |
| 5,192,291 A | 3/1993 | Pannek, Jr. |
| 5,226,909 A | 7/1993 | Evans et al. |
| 5,242,460 A | 9/1993 | Klein et al. |
| 5,350,390 A | 9/1994 | Sher |
| 5,358,478 A | 10/1994 | Thompson et al. |

(Continued)

OTHER PUBLICATIONS

PCT/US2017/026442, The International Search Report and the Written Opinion of the International Searching Authority, dated Jun. 23, 2017, 13pgs.

*Primary Examiner* — George J Ulsh

(57) ABSTRACT

A tissue removing catheter includes an apposition mechanism that selectively imparts an axially compressive load on the catheter body to bend the catheter and urge a tissue-removing element toward a blood vessel wall. The apposition mechanism can include one or more adjustment lines and an adjustment mechanism for selectively tensioning one of the adjustment lines to impart the compressive load on the catheter body. Two adjustment lines can have diametrically opposed positions and be wound onto a spool of the adjustment mechanism in opposite directions so that rotation of the spool simultaneously shortens one adjustment line and lengthens the other. The catheter body can have a more flexible bending segment adjacent the tissue-removing element to promote bending near the tissue-removing element operative to urge the tissue-removing element in apposition with the blood vessel.

22 Claims, 8 Drawing Sheets

(56) References Cited

U.S. PATENT DOCUMENTS

| | | | |
|---|---|---|---|
| 5,507,760 A | 4/1996 | Wynne et al. |
| 5,507,795 A | 4/1996 | Chiang et al. |
| 5,556,408 A | 9/1996 | Farhat |
| 5,569,277 A | 10/1996 | Evans et al. |
| 5,601,580 A | 2/1997 | Goldberg et al. |
| 5,620,456 A | 4/1997 | Sauer et al. |
| 5,776,156 A | 7/1998 | Shikhman |
| 5,857,982 A | 1/1999 | Milliman et al. |
| 6,053,923 A | 4/2000 | Veca et al. |
| 6,068,603 A | 5/2000 | Suziki |
| 6,110,127 A | 8/2000 | Suziki |
| 6,428,539 B1 | 8/2002 | Baxter et al. |
| 6,503,263 B2 | 1/2003 | Adams |
| RE38,018 E | 3/2003 | Anctil et al. |
| 6,579,298 B1 | 6/2003 | Bruneau et al. |
| RE38,335 E | 11/2003 | Aust et al. |
| 7,329,267 B2 | 2/2008 | Weber |
| 7,344,546 B2 | 3/2008 | Wulfmann et al. |
| 7,485,125 B2 | 2/2009 | Sjostrom |
| 7,520,886 B2 | 4/2009 | Surti |
| 7,635,340 B2 | 12/2009 | Vetter et al. |
| 7,699,790 B2 | 4/2010 | Simpson |
| 7,862,518 B2 | 1/2011 | Parihar |
| 7,918,803 B2 | 4/2011 | Ritchart et al. |
| 7,927,784 B2 | 4/2011 | Simpson |
| 7,951,161 B2 | 5/2011 | Bonnette et al. |
| 7,981,128 B2 | 7/2011 | To et al. |
| 8,012,164 B1 | 9/2011 | Donohoe et al. |
| 8,052,704 B2 | 11/2011 | Olson |
| 8,062,316 B2 | 11/2011 | Patel et al. |
| 8,070,762 B2 | 12/2011 | Escudero et al. |
| 2004/0006358 A1 | 1/2004 | Wulfman et al. |
| 2007/0055259 A1 | 3/2007 | Norton et al. |
| 2007/0276419 A1 | 11/2007 | Rosenthal |
| 2007/0282358 A1 | 12/2007 | Remiszewski et al. |
| 2008/0045986 A1 | 2/2008 | To et al. |
| 2008/0065124 A1 | 3/2008 | Olson |
| 2008/0140104 A1 | 6/2008 | Bender et al. |
| 2010/0198240 A1 | 8/2010 | Simpson et al. |
| 2011/0004107 A1 | 1/2011 | Rosenthal et al. |
| 2011/0087258 A1 | 4/2011 | Sluss |
| 2011/0130777 A1 | 6/2011 | Zhang et al. |
| 2011/0144673 A1 | 6/2011 | Zhang et al. |
| 2011/0152906 A1 | 6/2011 | Escudero et al. |
| 2011/0190801 A1 | 8/2011 | Mark et al. |
| 2011/0213363 A1 | 9/2011 | Cunningham et al. |
| 2011/0295242 A1 | 12/2011 | Spivey et al. |
| 2011/0301626 A1 | 12/2011 | To et al. |
| 2011/0306995 A1 | 12/2011 | Moberg |
| 2013/0131593 A1* | 5/2013 | Selkee ............ A61M 25/0136 604/95.04 |
| 2014/0221751 A1 | 8/2014 | Schwarz et al. |
| 2014/0222047 A1 | 8/2014 | Vreeman |
| 2016/0067457 A1 | 3/2016 | Selkee |

* cited by examiner

TISSUE-REMOVING CATHETER WITH ADJUSTMENT MECHANISM

FIELD

The present disclosure generally relates to a tissue-removing catheter.

BACKGROUND

Debulking or tissue-removing catheters are used to remove unwanted tissue from the body. As an example, atherectomy catheters are used to remove material from a blood vessel to open the blood vessel and improve blood flow through the vessel.

SUMMARY

In one aspect, a tissue-removing catheter includes first and second adjustment lines extending generally along a longitudinal axis of a catheter body at circumferentially spaced apart locations about the longitudinal axis. Each of the first and second adjustment lines have a distal end portion attached to the catheter body at respective first and second connection points adjacent the distal end portion of the catheter body, and an opposite proximal end portion. An adjustment mechanism is operatively connected to the proximal end portions of the first and second adjustment lines. The adjustment mechanism is selectively operable to decrease an effective length of the first adjustment line to bend the distal end portion of the catheter body in a first direction and urge the tissue-removing element in the first direction. The adjustment mechanism is selectively operable to decrease an effective length of the second adjustment line to bend the distal end portion of the catheter body in a second direction different than the first direction and urge the tissue-removing element in the second direction.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Embodiments of a tissue-removing catheter having improved radial tissue-removing positioning within a body lumen for removing tissue from body lumens of different sizes are disclosed. The illustrated catheter embodiments are particularly suitable for removing (e.g., excising) plaque tissue from a blood vessel (e.g., peripheral arterial or peripheral venous wall). Features of the disclosed embodiments, however, may also be suitable for treating chronic total occlusion (CTO) of blood vessels, particularly peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from, and penetrating occlusions in, blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 1:
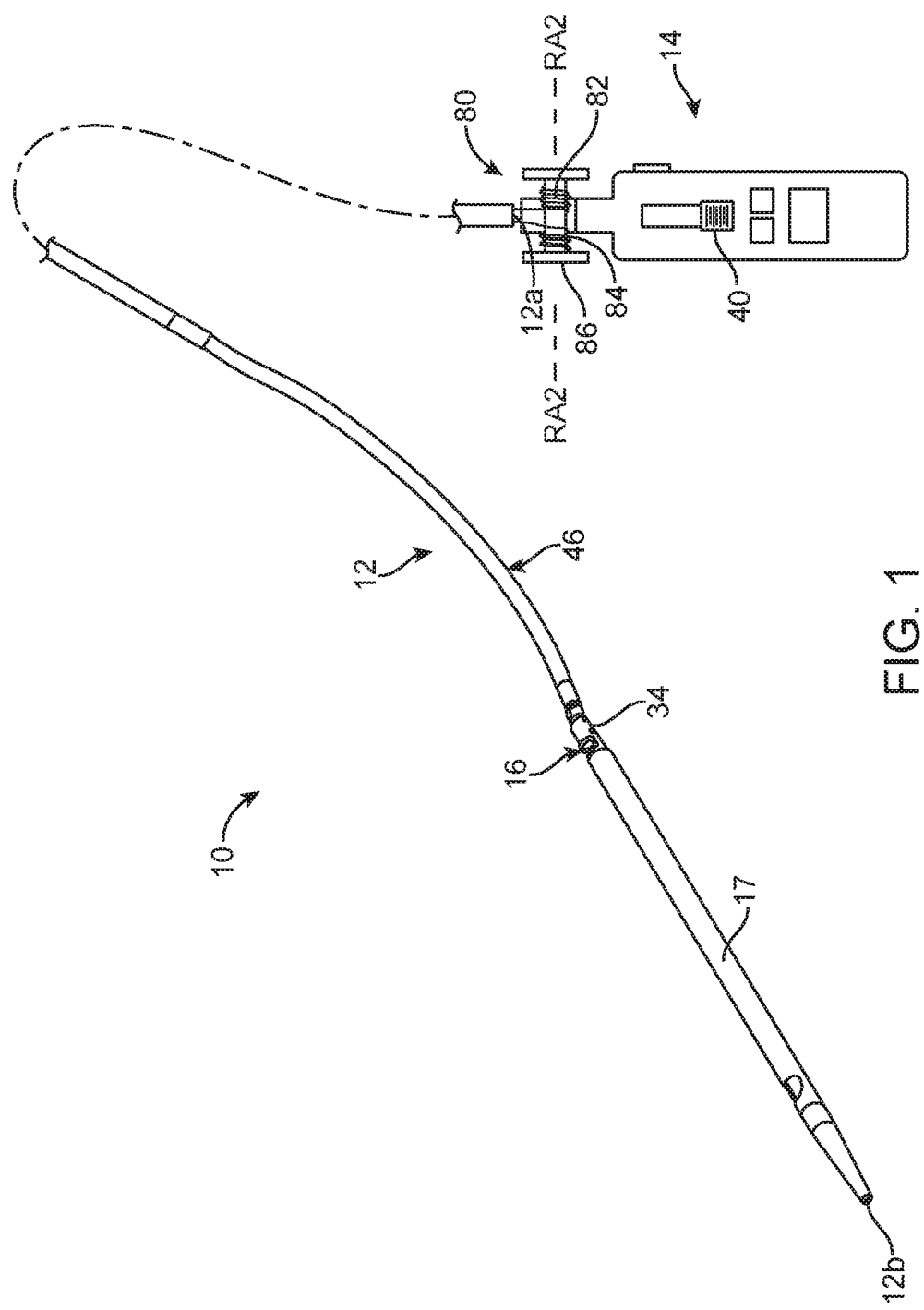
FIG. 1 is a perspective of a catheter body and a schematic representation of a handle, each of which is a part of a catheter.

Referring to FIG. 1, a tissue-removing catheter, in accordance with one or more embodiments of the present disclosure, is generally indicated at reference numeral 10. The catheter 10 comprises an elongate catheter body, generally indicated at 12, having opposite proximal and distal ends 12a, 12b, respectively, and a longitudinal axis CA (FIG. 3) extending between the proximal and distal ends. A handle or control unit, generally indicated at 14, is attachable to the proximal end 12a of the catheter body 12, although the handle may be fixedly attached to the catheter body in other embodiments. A tissue-removing element, generally indicated at 16, is located generally adjacent the distal end 12b of the catheter body 12. In the illustrated embodiment, the tissue-removing element 16 comprises a cutting element that is configured to remove (e.g., cut) tissue from the body lumen. The illustrated cutting element 16 is also configured to direct the removed tissue into a tissue container 17.

Figure 2:
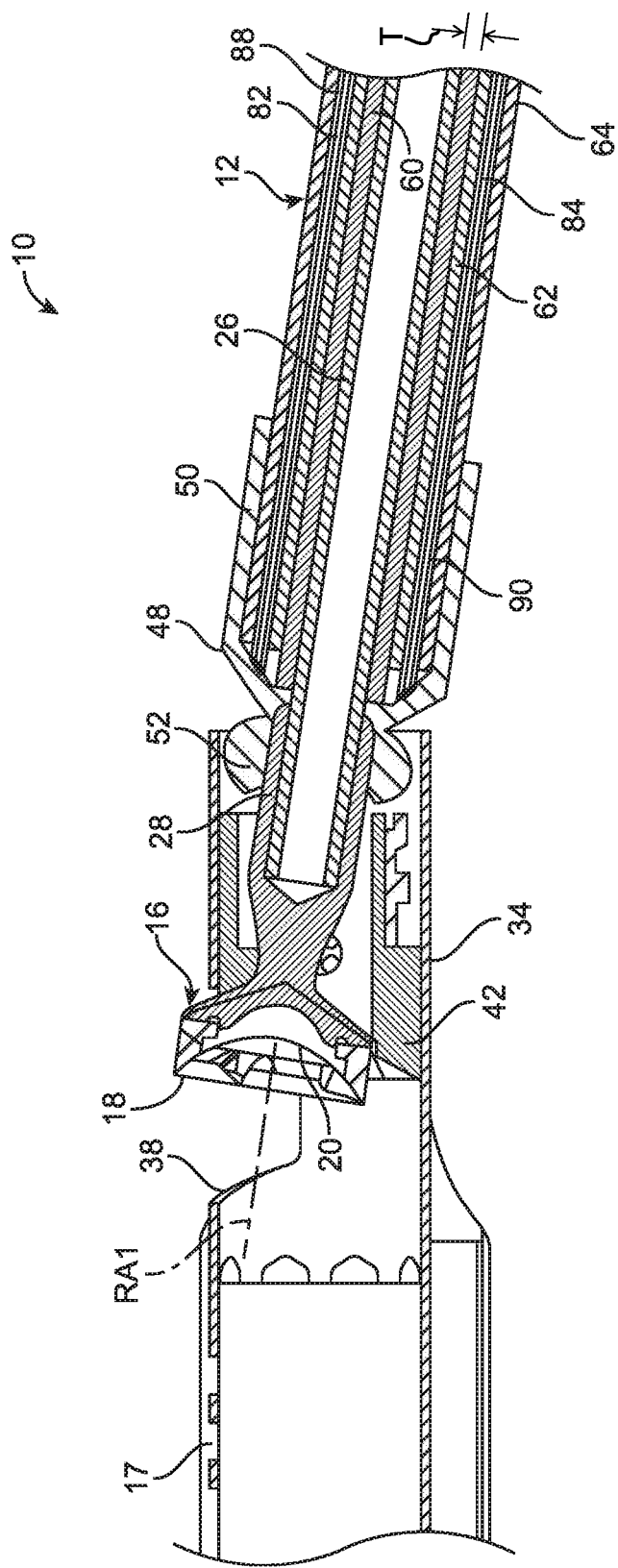
FIG. 2 is an enlarged fragmentary sectional view of the catheter body illustrating a tissue-removing element in a deployed position.

Referring to FIG. 2, in the illustrated embodiment, the cutting element 16 is rotatable about a rotation axis RA1 for cutting tissue. The illustrated cutting element 16 has a cutting edge 18 facing distally and extending circumferentially around the rotation axis RA1 and a cup-shaped surface 20 for directing removed tissue distally into the tissue container 17 of the catheter body 12. In other embodiments, the tissue-removing element may have other configurations for cutting tissue (e.g., the cutting edge may face proximally), or may be configured to remove tissue in other ways (e.g., the tissue-removing element may be configured to ablate tissue, or abrade tissue, or otherwise remove tissue from the body lumen). Moreover, the tissue-removing element may not be rotatable relative to the catheter body.

Referring still to FIG. 2, a tissue-removing driveshaft 26 is operatively connected to a stem 28 of the cutting element 16 (e.g., fixedly secured thereto) for imparting rotation to the cutting element. The tissue-removing driveshaft 26 (e.g., a coiled or helical driveshaft) extends through the catheter body 12 and is operatively connectable to an electric driveshaft motor, or other prime mover (not shown), in the handle 14 for driving rotation of the driveshaft, and in turn, driving rotation of the cutting element 16, relative to the catheter body. In the illustrated embodiment, the driveshaft 26 is movable longitudinally within the catheter body 12 to impart longitudinal movement of the cutting element 16 relative to the catheter body.

In the illustrated embodiment, the cutting element 16 is selectively movable relative to the catheter body 22 between a stowed position (not shown) and a deployed position (FIGS. 1 and 2). In the stowed position, the cutting element 16 is generally disposed in a tissue-removing housing 34 of the catheter body 12 to minimize the cross-sectional size of the catheter body. This allows the catheter body 12 to pass more easily through the blood vessel during insertion. In the deployed position, the cutting element 16 extends radially through a cutting window 38 located adjacent the distal end 12b of the catheter body 12. The cutting window 38 has a circumferential position with respect to the longitudinal axis CA of the catheter body 22 (e.g., at the top of the catheter body as illustrated in FIG. 2). Thus, when the cutting element 16 is deployed, it extends radially from the longitudinal axis CA generally at the circumferential position of the cutting window 38. As explained below, the catheter 10 is configured to selectively bend the catheter body 12 in a bending direction that urges a distal end portion of the catheter body in the circumferential direction of the cutting window, to urge the deployed cutting element 16 radially outward.

In the illustrated embodiment, longitudinal movement of the cutting element 16 relative to the catheter body 12 actuates selective deployment and storage of the cutting element relative to the tissue-removing housing 34. To deploy the cutting element 16, the driveshaft 26 is moved proximally relative to the catheter body 12, such as by moving a lever or other actuator 40 (FIG. 1) on the handle 14 that is operatively connected to the driveshaft, to impart proximal movement of the cutting element 16 relative to the housing 34. Referring to FIG. 2, as the cutting element 16 moves proximally, the cutting element, which acts as a cam, engages and moves longitudinally along an internal cam follower 42 of the housing 34, causing the housing to pivot about a pivot axis PA (FIG. 3) and the cutting element to extend partially out of the window 38. To return the cutting element 16 to its stored, non-deployed position, the driveshaft 26 is moved distally, such as by moving the actuator 40 distally, to impart distal movement of the cutting element 16 along the cam follower 42. Distal movement of the cutting element 16 causes the housing 34 to pivot or deflect back about the pivot axis PA so that the cutting element is received in the housing 34 and does not extend outside the window 38. It is understood that a catheter 10 constructed according to the principles of the present disclosure may include other types of deployment mechanisms or may not include a deployment mechanism (e.g., the cutting element or other functional element may always be deployed or may remain within the catheter body). For example, the cutting element may be exposed through the distal end of the catheter body.

Figure 3:
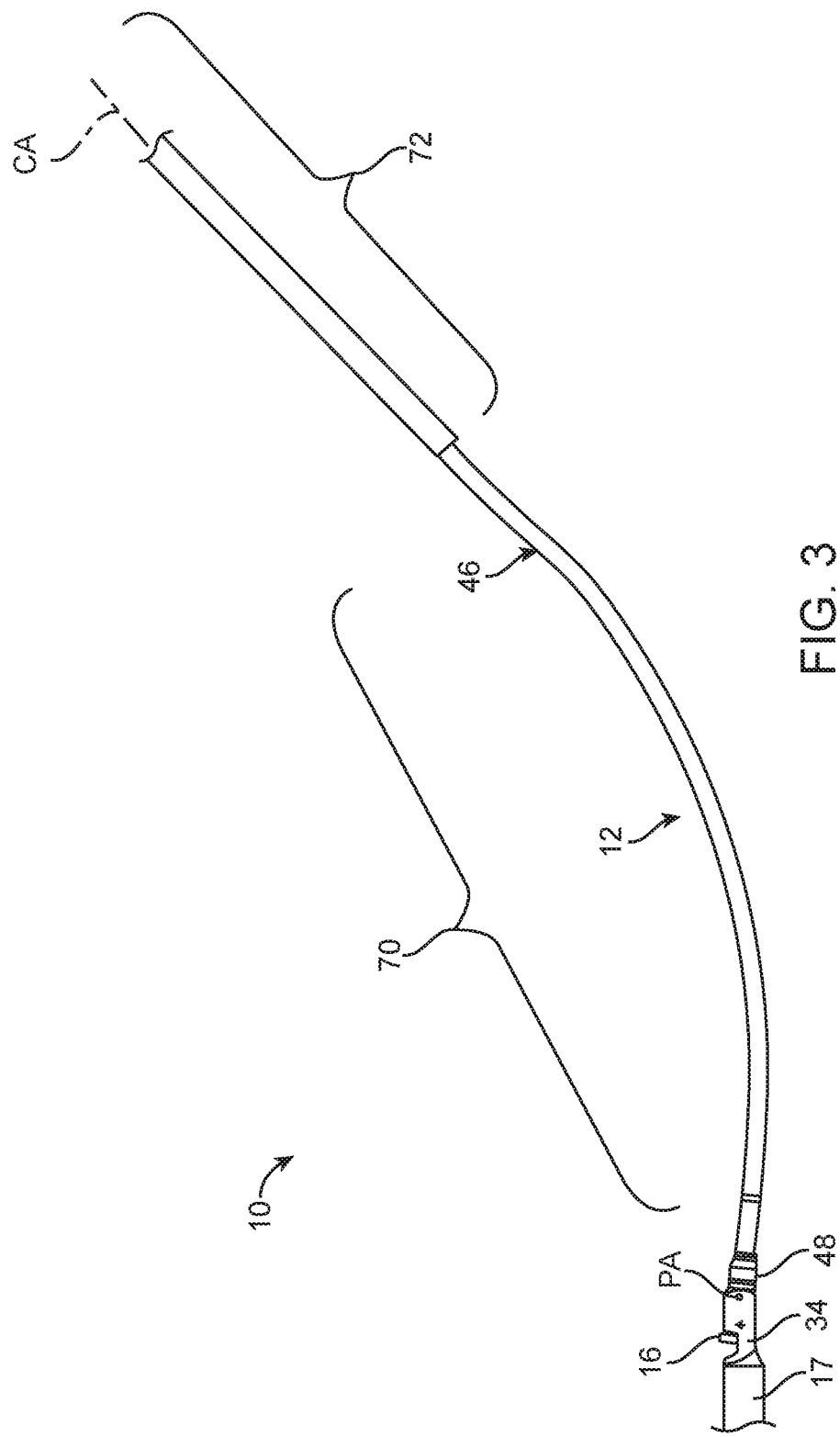
FIG. 3 is an enlarged fragmentary side elevation of the catheter body.
Figure 4:
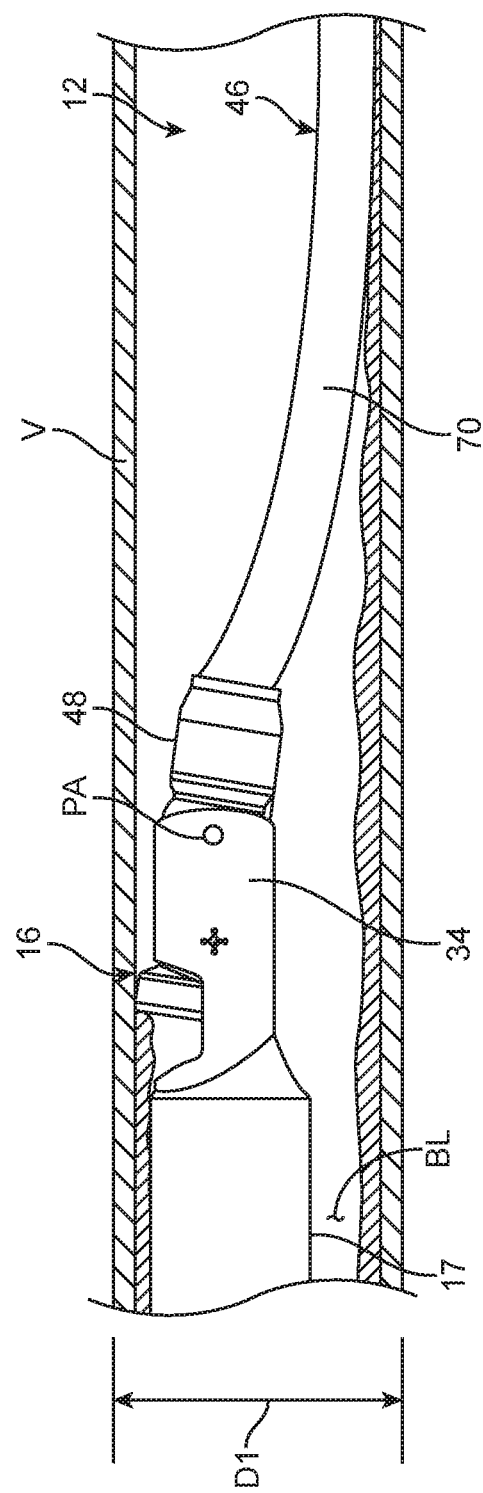
FIG. 4 is an enlarged fragmentary side elevation of the catheter body received in a blood vessel shown in section.

Referring to FIG. 3, the tissue-removing housing 34 is pivotably connected to a flexible torque shaft, generally indicated at 46, that extends proximally along the longitudinal axis CA from adjacent the tissue-removing housing to the proximal end 12a of the catheter body 12. The torque shaft 46 is suitably flexible for navigating the catheter body 12 through tortuous paths within a body lumen BL defined by a blood vessel V (FIG. 4). Referring to FIG. 2, a rigid connector 48 that comprises a proximal collar portion 50 and distal ball joint portion 52 is secured to the distal end portion of the torque shaft 46. The ball joint portion 52 is pivotably received in the open proximal end portion of the tissue-removing housing 34 (e.g., using a pin) to allow pivoting of the housing with respect to the connector 48. Suitably, the connector 48 is hollow to allow the drive shaft 26 to extend axially through the connector for operative connection with the cutting element 16.

Figure 5:
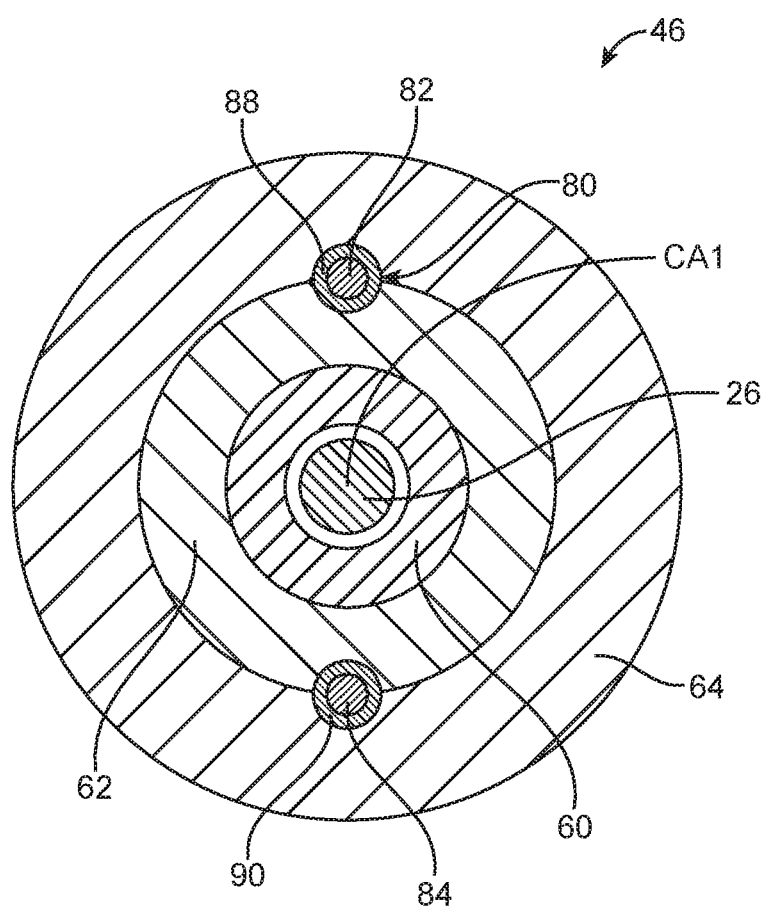
FIG. 5 is a section of a torque shaft of the catheter body.

Referring to FIG. 5, the torque shaft 46 includes a support coil 60 that is wound around the drive shaft 26 and extends along the longitudinal axis CA from adjacent the distal end of the torque shaft to adjacent the proximal end. The coil 60 is suitably configured to transmit torque from its proximal end toward its distal end. The support coil 60 may be formed from stainless steel or other materials. A reinforcement sleeve 62 extends circumferentially around the coil 60 and extends axially from adjacent the distal end of the torque shaft 46 to adjacent the proximal end. In one or more embodiments, the reinforcement sleeve 62 is formed from braided stainless steel, but other materials and constructions may also be used in other embodiments. An outer fluid-impermeable jacket 64 extends circumferentially around the reinforcement sleeve and extends along the longitudinal axis CA from adjacent the distal end of the torque shaft 46 to adjacent the proximal end. In one or more embodiments, the jacket 64 comprises a flexible polymer material, such as a thermoplastic elastomer (e.g., polyether block amide), though other materials may also be used in other embodiments. In the illustrated embodiment, the drive shaft 26, the support coil 60, the reinforcement sleeve 62, and the jacket 64 are disposed in concentric relationship about the longitudinal axis CA. But in other embodiments, one or more components could be radially offset from the longitudinal axis CA.

Referring again to FIG. 3, the torque shaft 46 includes a bending longitudinal portion 70 and a proximally-adjacent longitudinal portion 72 that is immediately proximal the bending longitudinal portion. The bending longitudinal portion 70 extends proximally along the longitudinal axis CA, from a distal end secured to the collar portion 50 of the connector 48, to a proximal end that is spaced apart from the proximal end 12a of the catheter body 12. The proximally-adjacent longitudinal portion 72 extends proximally along the longitudinal axis CA from adjacent the proximal end of the bending longitudinal portion 70 toward the proximal end 12a of the catheter body 12. The torque shaft 46 is constructed so that the bending longitudinal portion 70 has a bending stiffness that is less than the proximally-adjacent longitudinal portion 72 (e.g., the bending longitudinal portion is more flexible than the proximally-adjacent longitudinal portion 72). Thus, when a radial bending force is imparted on the catheter body 12, the torque shaft 46 preferentially bends along the bending longitudinal portion 70 instead of the proximally-adjacent longitudinal portion 72. As explained below, since the bending longitudinal portion 70 is located adjacent the cutting element 16, radial bending of the bending longitudinal portion can direct the cutting element 16 in apposition toward a portion of the blood vessel V as shown in FIG. 4 to operatively position the cutting element for removing tissue from the periphery of the body lumen BL.

There are a number of ways of constructing the torque shaft 46 so that the bending longitudinal portion 70 has a bending stiffness less than in the proximally-adjacent longitudinal portion 72. In one or more embodiments, the jacket 64 may have different bending stiffnesses in the bending longitudinal portion 70 and proximally-adjacent longitudinal portion 72. For example, the jacket 64 comprises a material in the bending longitudinal portion 70 having a flexural modulus less than flexural modulus of material in the proximally-adjacent longitudinal portion 72. In one example, the jacket 64 may have a first shore hardness at the bending longitudinal portion 70 and a second shore hardness in the proximally-adjacent longitudinal portion, and the first shore hardness is less than the second shore hardness. Additionally, or alternative embodiment, the braided reinforcement sleeve 62 may have a lower bending stiffness in the bending longitudinal portion 70 than in the proximally-adjacent longitudinal portion 72. For example, the sleeve 62 comprises a braided material that has a first pick rate at the bending longitudinal portion 70 and that has a second pick rate at the proximally-adjacent longitudinal portion 72, and the first pick rate is less than the second pick rate. Additionally, or in an alternative embodiment, the support coil 60 has different bending stiffnesses in the bending longitudinal portion 70 and proximally-adjacent longitudinal portion 72. For example, the support coil 60 comprises material along the bending longitudinal portion 70 that has a flexural modulus less than material along the proximally-adjacent longitudinal portion 72. In the same or alternative example, the support coil 60 has a radial thickness T (FIG. 2), and the thickness T is a first radial thickness along the bending longitudinal portion 70 and a second, smaller radial thickness along the proximally-adjacent longitudinal portion 72. In still another embodiment, a relatively rigid reinforcing member is secured to the torque shaft 46 along the proximally-adjacent longitudinal portion, but not along the bending longitudinal portion. Still other suitable ways of constructing the torque shaft so that the bending longitudinal portion has a bending stiffness less than the bending stiffness of the proximally-adjacent longitudinal portion 72 may be used in other embodiments.

Referring again to FIG. 1, the catheter 10 includes an apposition mechanism, generally indicated at 80, configured to selectively bend the catheter body 12 in a generally radial direction relative to the longitudinal axis CA to direct the cutting element 16 toward a peripheral portion of the body lumen BL defined by the blood vessel V. In the illustrated embodiment, the apposition mechanism 80 is configured to selectively bend the bending longitudinal portion 70 of the catheter body 12 from a straight configuration to a bent configuration, and to selectively straighten the bending longitudinal portion from the bent configuration to the straight configuration. In one or more embodiments, the catheter body 12 may be constructed to be resiliently biased toward the configuration in which the bending longitudinal portion 70 is slightly curved. As shown in FIG. 4, in one or more embodiments, after the catheter 10 is inserted in the body lumen BL, the apposition mechanism 80 selectively urges a portion of the bending longitudinal portion 70 into operative engagement with a peripheral wall of the blood vessel V (the bottom portion of the bending longitudinal portion 70 as illustrated in FIG. 4). The bending longitudinal portion 70 extends distally from the point of engagement with the wall of the blood vessel V diametrically across the body lumen BL to maintain the cutting element 16 in operative engagement with a diametrically opposed portion of the blood vessel wall V. It will be understood that the cutting element 16 and/or torque shaft 46 can operatively engage a wall of a blood vessel V when it directly contacts the blood vessel or contacts tissue that is attached to the blood vessel.

Referring again to FIG. 5, the apposition mechanism 80 includes first and second adjustment lines 82, 84, which extend along the catheter body 12 at circumferentially spaced apart locations about the longitudinal axis CA, and an adjustment mechanism 86. For example, the first and second adjustment lines 82, 84 are spaced apart in diametrically opposed relationship about the longitudinal axis CA. Each of the adjustment lines 82, 84 extends from a distal end portion (e.g., adjacent the bending longitudinal portion 70) that is attached to the catheter body 12 at the collar portion 50 of the rigid connector 48 as shown in FIG. 2, to a proximal end portion that is connected to the adjustment mechanism 86, which may be mounted on the handle 14 as shown in FIG. 1. The first and second adjustment lines 82, 84 are movable longitudinally with respect to the catheter body 12, as explained in more detail below. Suitably, each of the adjustment lines 82, 84 comprises a flexible cable or wire, such as a stainless steel wire, that is generally not longitudinally elastic or deformable (i.e., generally non-deformable along its length during use).

Referring still to FIG. 5, the adjustment lines 82, 84 are movable relative to the torque shaft 46 along the longitudinal axis CA to cause bending of the catheter body 12 at the bending longitudinal portion 70. In the illustrated embodiment, each of the adjustment lines 82, 84 is slidably received in a respective tube 88, 90. Each tube 88, 90 is positioned radially between the jacket 64 and the reinforcing sleeve 62. Suitably, the tubes 88, 90 may comprise a polymer material that has a low friction surface to allow for relatively free sliding of the adjustment lines 82, 84 through the sleeves. The adjustment lines 82, 84 could be supported on the torque shaft 46 for movement along the length of the torque shaft in other ways in other embodiments.

Referring to FIG. 2, the distal end portion of each of the adjustment lines 82, 84 is secured to the rigid connector 48 at a respective connection point so that either adjustment line can impart an axially compressive load on the catheter body 12 when a tensile force is imparted on the proximal end portion thereof. The connector 48 is spaced apart proximally from the cutting window 38 so that each adjustment line 82, 84 imparts axially compressive loads on the torque shaft 46. As discussed above, each of the adjustment lines 82, 84 is spaced apart radially from the longitudinal axis CA of the catheter body 12 at an opposite circumferential position. When only one of the adjustment lines 82, 84 imparts an axially compressive load on the torque shaft 46 (i.e., where one of the adjustment lines is tensioned but not the other), it creates an imbalance of axial forces on the catheter that causes a bending moment. The imbalanced axially compressive load bends the torque shaft 46 radially in a circumferential direction aligned with the circumferential position of the tensioned adjustment line about the longitudinal axis CA. As explained above, since the bending longitudinal portion 70 of the torque shaft 46 is more flexible than the proximally-adjacent longitudinal portion 72, bending occurs along the bending longitudinal portion to urge the distal end portion 12b of the catheter toward the periphery of the body lumen BL. In the illustrated embodiment, the first adjustment line 82 is circumferentially aligned with the cutting window 38 about the longitudinal axis CA, as shown in FIG. 4. Thus, when the adjustment line 82 is tensioned, it imparts an axially compressive load on the torque shaft 46 that bends the bending longitudinal portion 70 to urge the deployed cutting element 16 in apposition with a portion of the blood vessel V as shown in FIG. 4, thereby operatively positioning the cutting element to remove tissue from the periphery of the body lumen BL.

Referring still to FIG. 4, when the adjustment line 82 is tensioned to urge the deployed cutting element 16 in apposition with the perimeter of the body lumen BL, the cutting element and the bending longitudinal portion 70 of the torque shaft 46 contact generally diametrically opposed portions of the blood vessel V. That is, in the operative position, the cutting element 16 is radially urged toward engagement with the blood vessel V at a first point of contact and the bending longitudinal portion 70 of the torque shaft 46 is urged toward engagement with the blood vessel at a second point of contact that is spaced apart from the first point of contact by a diameter D of the blood vessel V. When the catheter 10 has this configuration (i.e., where the cutting element 16 and the bending longitudinal portion 70 engage diametrically opposed portions of the blood vessel V), the catheter has an effective diameter that is the same as the diameter D of the blood vessel.

By adjusting the tension in the adjustment line 82, the apposition mechanism 80 can bend the catheter body 12 to have a desired effective diameter D. Moreover, the apposition mechanism 80 can selectively bend the catheter body 12 through a range of motion that corresponds with a range of effective diameters D suitable for blood vessels V of substantially different diameters. As the amount tension in the adjustment line 82 increases, the amount of bending in the bending longitudinal portion 70 likewise increases. For blood vessels with relatively small diameters D, the apposition mechanism 80 can impart a relatively small tension on the adjustment line 82 to maintain the cutting element 16 in operative engagement with the periphery of the blood vessel V. For blood vessels with relatively large diameters D, the apposition mechanism 80 can impart a relatively large tension on the adjustment line 82 to maintain the cutting element 16 in operative engagement with the blood vessel V. In one or more embodiments, the apposition mechanism 80 can bend the torque shaft 46 through a range of motion that corresponds with a range of effective diameters D of from less than or equal to about 2 mm to at least about 8 mm. Thus, it can be seen that the apposition mechanism 80 can be used to operatively position a single catheter 10 in blood vessels V that vary substantially in cross-sectional size.

By adjusting the tension in one or both of the adjustment lines 82, 84 the apposition mechanism 80 can also selectively configure the distal end portion of the catheter body 12 in a straight or erect configuration. For example, in one embodiment, the distal end portion 12b of the catheter body 12 is resiliently biased toward a configuration in which it curves radially in the circumferential direction of the adjustment line 82. By maintaining a tension on the second adjustment line 84 in this embodiment, the bending longitudinal portion 70 of the catheter body 12 can be maintained in a straightened or erect configuration. In another embodiment, the distal end portion 12b of the catheter body 12 is compliantly flexible when no axially compressive load is imparted thereupon, and the apposition mechanism 80 can selectively tension both of the adjustment lines 82, 84 at the same time to straighten the bending longitudinal portion 70 of the catheter body. The apposition mechanism 80 is configured to resist bending of the bending longitudinal portion 70 from the straightened configuration. This is thought to have application for tissue-removing catheters used for crossing a chronic total occlusion, for example, with a tissue-removing element operatively mounted at the distal tip of the catheter for exposure through the distal end of the catheter body (not shown). By selectively maintaining the distal end portion 12b of the catheter body in an erect configuration during crossing of a chronic total occlusion, the leading tissue-removing element can engage the tissue with greater axial force without bending, to more effectively bore through and cross the tissue.

Figure 6:
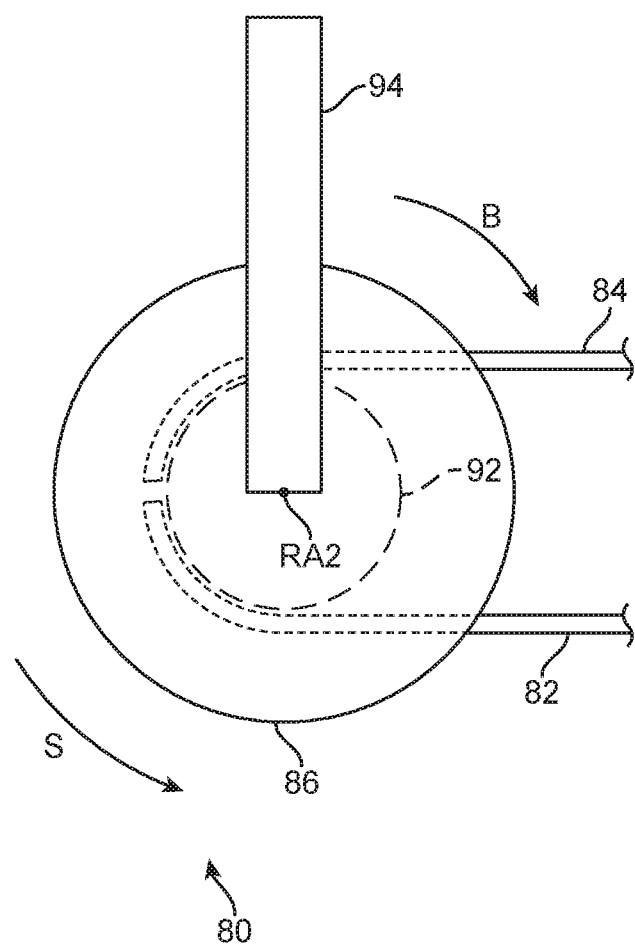
FIG. 6 is a fragmentary schematic representation of a portion of an apposition mechanism of the catheter, including an adjustment mechanism and adjustment lines that extend into the catheter body.

Referring to FIG. 6, the adjustment mechanism 86 is operatively connected to the proximal end portions of the first and second adjustment lines 82, 84 to selectively adjust the effective lengths of the adjustment lines extending between the adjustment mechanism and the connector 48 and to thereby impart a radially offset axial compression load on the torque shaft 46. In the illustrated embodiment, the adjustment mechanism 86 comprises a spool 92. A lever 94 is configured to selectively rotate the spool 92 about an axis of rotation RA2 oriented transverse to (e.g., perpendicular to) the longitudinal axis CA of the catheter body 12. The lever 94 can be actuated to rotate the spool 92 about the axis of rotation RA2 in a bending direction B or a straightening direction S. When the spool 92 is rotated, the effective length of one of the adjustment lines 82, 84 extending between the adjustment mechanism 86 and the connector 48 is decreased and the length of the other adjustment line extending between the adjustment mechanism and the connector is increased by the same amount. Shortening the effective length of either of the adjustment lines 82, 84 imparts a tension on the adjustment line and an axially compressive load on the catheter body 12. In one or more embodiments, the adjustment mechanism 86 includes a tensioner (e.g., a ratcheting mechanism, frictional tensioner, etc.) configured to maintain a tension on the adjustment line 82, 84 (e.g., maintain the circumferential position of the lever 84) after the tension has been applied without further input from the user. The user can subsequently use the adjustment mechanism 86 to change the tension on the adjustment lines 82, 84, for example, by rotating the lever 94 about the axis of rotation RA2.

When the spool 92 is rotated in the bending direction B, a portion of the first adjustment line 82 is wound onto the spool and a portion of the second adjustment line 84 is let off of the spool. This simultaneously decreases the effective length of the first adjustment line 82 extending between the spool 92 and the connector 48 and increases the effective length of the second adjustment line 84 extending between the spool and the connector. Thus, the first adjustment line 82 is tensioned to impart an axially compressive load on the torque shaft 46 at one circumferential position. And by increasing the effective length of the second adjustment line 84, the second adjustment line allows an opposed portion of the torque shaft to freely expand in the lengthwise direction without imparting an axially compressive load on the torque shaft. Since the first adjustment line 82 is circumferentially aligned with the cutting window 38, the first and second adjustment lines 82, 84 work in concert to bend the torque shaft 46 along the bending longitudinal portion 70 to urge the deployed cutting element 16 in apposition with the periphery of the blood vessel V as shown in FIG. 4.

Referring again to FIG. 6, when the spool 92 is rotated in the straightening direction S, a portion of the second adjustment line 84 is wound onto the spool and a portion of the first adjustment line 82 is let off of the spool. This simultaneously increases the effective length of the first adjustment line 82 extending between the spool 92 and the connector 48 and decreases the effective length of the second adjustment line 84 extending between the spool and the connector. The second adjustment line 84 is tensioned to impart an axially compressive load on the torque shaft 46 at one circumferential position. When this occurs after the torque shaft 46 has been bent by rotating the spool 92 in the bending direction B, the axially compressive load imparted by the second adjustment line 84 forces the catheter body 12 to straighten, drawing the cutting element 16 radially inward of the blood vessel V. By simultaneously increasing the effective length of the first adjustment line 82, the first adjustment line allows the circumferentially aligned portion of the torque shaft 46 to freely expand in the lengthwise direction without imparting an axially compressive load on the torque shaft. In one or more embodiments, the effective lengths of the first and second adjustment lines 82, 84 are generally equal when the distal end portion of the catheter body is in the straight configuration. Thus, it can be seen that the adjustment mechanism 86 provides an active system for both bending the catheter body 12 to operatively position the cutting element 16 in apposition with the blood vessel V and subsequently straightening the catheter body to allow for removal of the catheter 10 from the body lumen BL.

Although the illustrated adjustment mechanism 86 uses a lever-controlled spool 92, other adjustment mechanisms for simultaneously adjusting the effective lengths of the first and second adjustment lines may be used in other embodiments. In still other embodiments, the adjustment mechanism may separately and/or sequentially adjust the effective lengths of the first and separate adjustment lines to bend and straighten the catheter body.

In use, the catheter body 12 is inserted into the body lumen BL, for example, using a guide wire (not shown). The catheter body 12 travels axially through the body lumen BL until the cutting element 16 is positioned adjacent a lesion or other tissue formation in the body lumen. There, the user can activate the apposition mechanism 80 to urge the cutting window 38 and cutting element 16 in apposition with a perimeter portion of the blood vessel V. The user uses the lever 94 to rotate the spool 92 in the bending direction B, which decreases the effective length of the first adjustment line 82 extending between the spool 92 and connector 48 and increases the same effective length of the second adjustment line 84, thereby imparting a radially offset compression load on the torque shaft 46 that is circumferentially aligned with the first adjustment line 82 and cutting window 38 about the longitudinal axis CA. The axially compressive load bends the torque shaft 46 along the bending longitudinal portion 70 to urge the cutting window 38 and the cutting element 16 in apposition with the blood vessel V and to urge the bending longitudinal portion in apposition with a diametrically opposed portion of the blood vessel.

The user then deploys the cutting element 16 and activates the motor (not shown) to impart rotation upon the drive shaft 26 and thereby rotate the deployed cutting element about the axis of rotation RA1. While the cutting element 16 rotates, the user advances the catheter body 12 axially through the body lumen BL and the cutting element cuts the tissue. The cut tissue deflects off of the cup-shaped surface 20 as the catheter 10 advances, which directs the cut tissue into the tissue-collection container 17. If the diameter of the body lumen changes across the length of the lesion, the user can adjust the apposition mechanism 80 to maintain the cutting element 16 in the operative position (e.g., increasing the effective diameter D of the catheter 10 by rotating the spool 92 in the bending direction B or decreasing the effective diameter of the catheter 10 by rotating the spool in the straightening direction S).

When the desired tissue has been removed from the body lumen BL, the catheter 10 can be disengaged from the blood vessel V by rotating the spool in the straightening direction S. This decreases the effective length of the second adjustment line 84 extending between the spool 92 and the connector 48 and increases the same effective length of the first adjustment line 82. The net effect imparts an axially compressive load on the torque shaft 46 at the second adjustment line 84, which actively straightens the catheter body 12 and decreases the effective diameter D of the catheter 10. When the catheter body 12 is straightened, the catheter 10 can be removed by withdrawing the catheter body from the body lumen BL.

Figure 7:
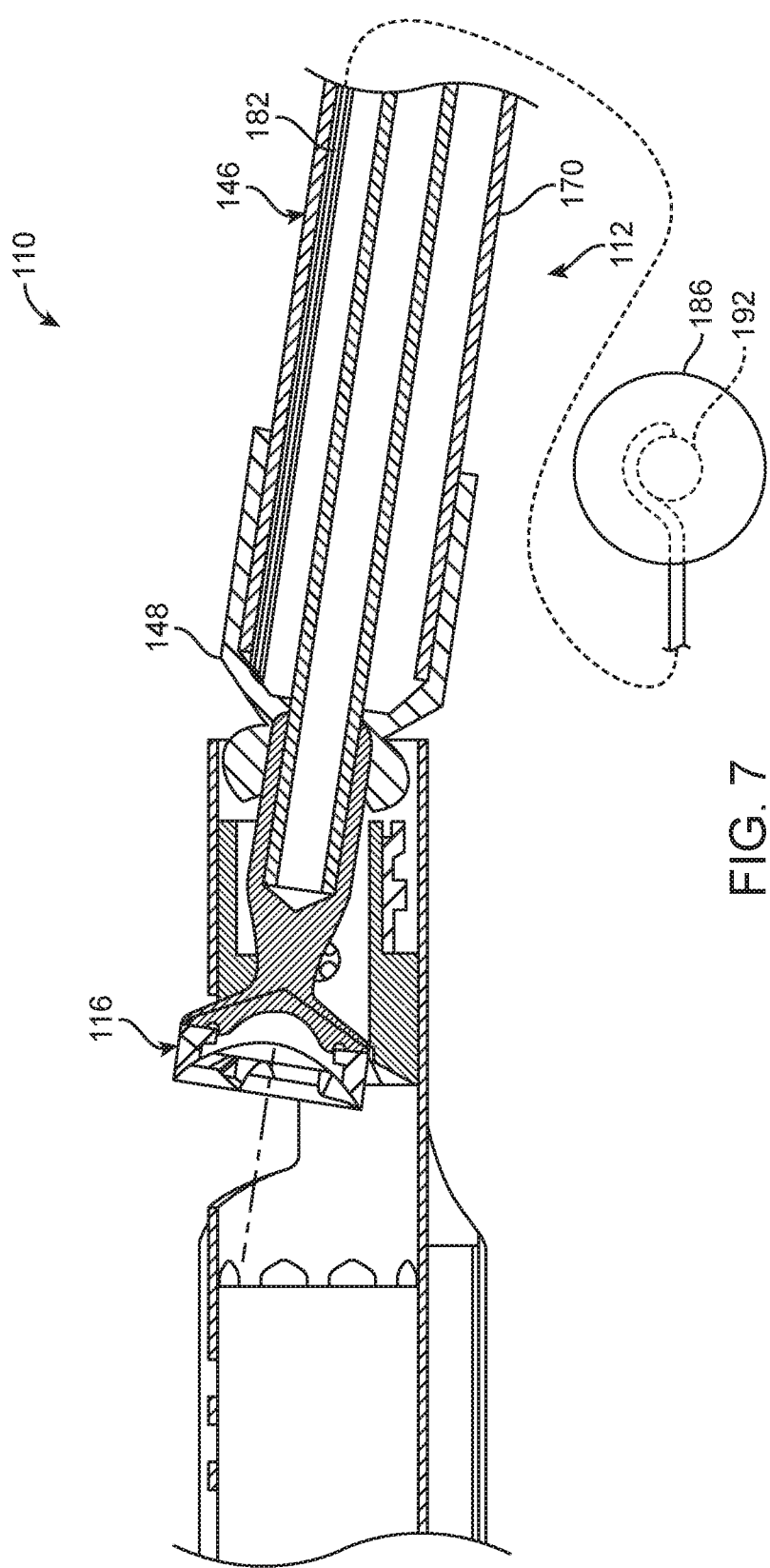
FIG. 7 is an enlarged fragmentary sectional view similar to FIG. 2 of a catheter body of another embodiment of a tissue-removing catheter and a schematic representation of an adjustment mechanism of an apposition mechanism of the catheter.

Referring to FIG. 7, in another embodiment, a catheter, generally indicated at 110, includes an apposition mechanism that includes only a single adjustment line 182. The catheter 110 is substantially similar to the catheter 10, and corresponding parts are given corresponding reference numbers, plus 100. In this embodiment, the catheter body 112 is constructed to be resiliently biased toward a straightened configuration. The adjustment line 182 is circumferentially aligned with the cutting window 138 to bend the bending longitudinal portion 170 of the torque shaft 146 to urge the deployed cutting element 116 toward apposition with a peripheral portion of the blood vessel V when the adjustment line 182 is tensioned. As above, the adjustment line 182 can be selectively tensioned by shortening the effective length of the adjustment line extending between the connector 148 and the adjustment mechanism 186 using a spool 192. To straighten the catheter body 112 after bending, the spool is rotated in the opposite direction to increase the effective length of the adjustment line 182 extending between the connector 148 and the adjustment mechanism 186. As the axially compressive load on the torque shaft 148 decreases, the catheter body 112 resiliently returns toward the straightened configuration.

Figure 8:
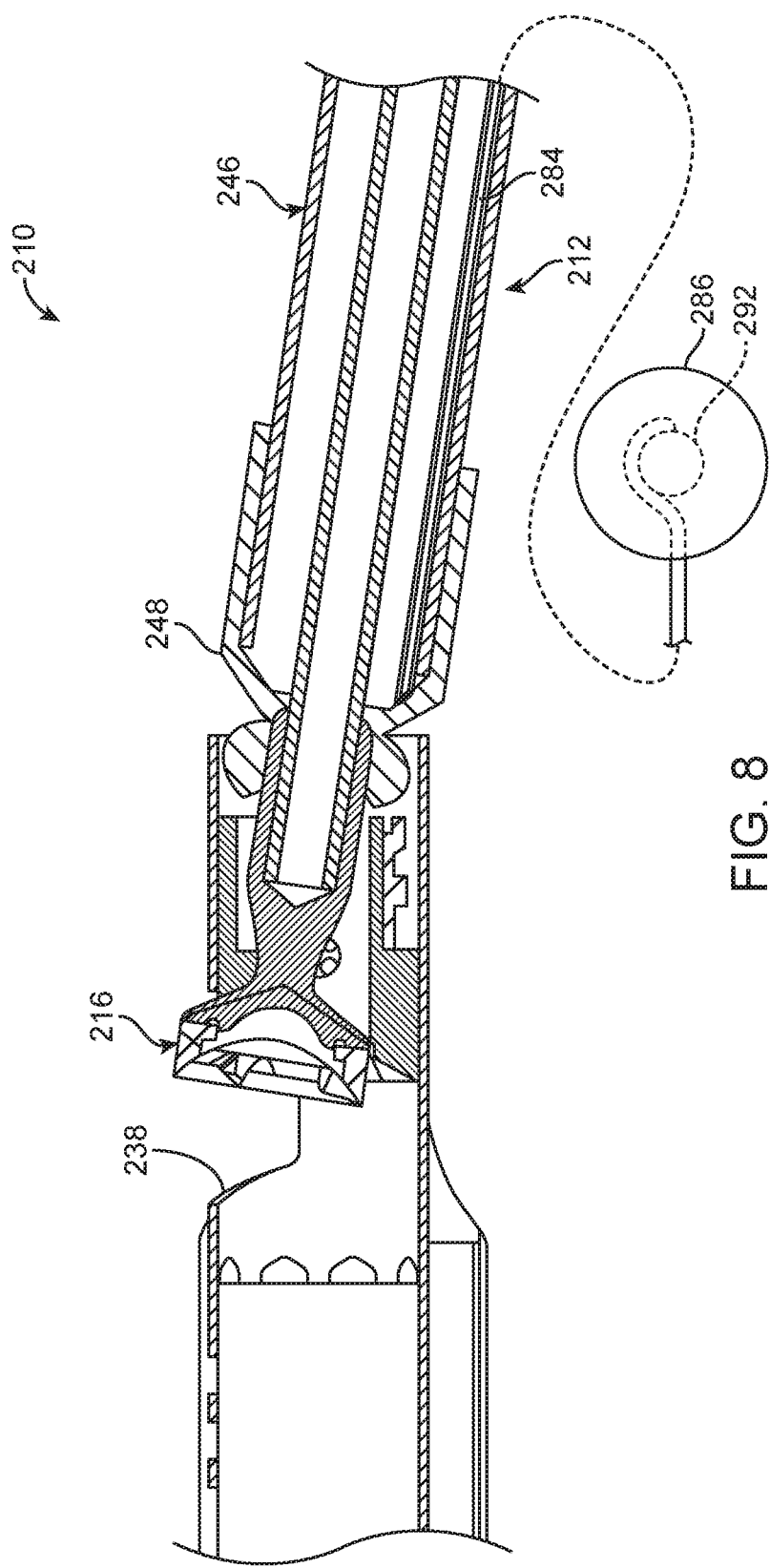
FIG. 8 is an enlarged fragmentary sectional view similar to FIGS. 2 and 7 of a catheter body of another embodiment of a tissue-removing catheter and a schematic representation of an adjustment mechanism of an apposition mechanism of the catheter.

Referring to FIG. 8, in yet another embodiment, a catheter, generally indicated at 210, includes an apposition mechanism that includes a single adjustment line 284 spaced apart in diametrically opposed relationship with a cutting window 238 about a longitudinal axis. The catheter 210 is substantially similar to the catheter 110, and corresponding parts are given corresponding reference numbers, plus 100. Unlike the catheter 110, the catheter body 212 of the catheter 210 is resiliently biased toward a substantially bent configuration (not shown). Thus, prior to inserting the catheter body into the body lumen BL, the adjustment mechanism 286 is used to rotate the spool 292 in the straightening direction. This winds the adjustment line 284 onto the spool 292 to shorten the effective length of the adjustment line extending between the spool and the connector 248 and imparts an axially compressive load on the torque shaft 246 that is radially offset from the longitudinal axis in the circumferential direction of the adjustment line. The compressive load straightens the pre-bent catheter body 212 to allow for passage through the body lumen. When the cutting element 216 is aligned with a tissue formation for removal, the spool 292 can be rotated in the bending direction to release the axial compression and allow the torque shaft 246 to resiliently return toward its pre-bent configuration, thereby urging the cutting element in apposition with the blood vessel V.

Having described the invention in detail, it will be apparent that modifications and variations are possible without departing from the scope of the invention defined in the appended claims.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A tissue-removing catheter comprising:
an elongate catheter body configured for insertion into a body lumen of a subject, the catheter body having a proximal end portion, an opposite distal end portion, and a longitudinal axis extending between the distal and proximal end portions;
a tissue-removing element located adjacent the distal end portion of the catheter body configured to remove tissue from the body lumen;
first and second adjustment lines extending along the catheter body at circumferentially spaced apart locations about the longitudinal axis, the first and second adjustment lines having distal end portions attached to the catheter body at respective first and second connection points adjacent the distal end portion of the catheter body, and the first and second adjustment lines having opposite proximal end portions; and
an adjustment mechanism operatively connected to the proximal end portions of the first and second adjustment lines, wherein the adjustment mechanism is selectively operable to decrease an effective length of the first adjustment line extending between the first connection point and the adjustment mechanism to bend the distal end portion of the catheter body in a first direction and urge the tissue-removing element in the first direction, wherein the adjustment mechanism is selectively operable to decrease an effective length of the second adjustment line extending between the second connection point and the adjustment mechanism to bend the distal end portion of the catheter body in a second direction different than the first direction and urge the tissue-removing element in the second direction;
wherein the distal end portion includes a bending longitudinal portion and a proximally-adjacent longitudinal portion that is immediately proximal to the bending longitudinal portion;
wherein the catheter body includes a drive shaft extending along the longitudinal axis and a jacket extending circumferentially around the drive shaft;
wherein the catheter body further includes a support coil received in the jacket and extending circumferentially around the drive shaft; and
wherein the support coil is stiffer along the proximally-adjacent longitudinal portion than along the bending longitudinal portion such that the bending longitudinal portion of the catheter body has a bending stiffness that is less than a bending stiffness of the proximally-adjacent longitudinal portion of the catheter body.

2. A tissue-removing catheter as set forth in claim 1, wherein the adjustment mechanism is operable to increase said effective length of the first adjustment line when decreasing said effective length of the second adjustment line, wherein the adjustment mechanism is operable to increase said effective length of the second adjustment line when decreasing said effective length of the first adjustment line.

3. A tissue-removing catheter as set forth in claim 2, wherein the adjustment mechanism is configured to simultaneously adjust said effective lengths of the first and second adjustment lines.

4. A tissue-removing catheter as set forth in claim 3, wherein the adjustment mechanism is configured to simultaneously adjust said effective lengths of the first and second adjustment lines by the same amount.

5. A tissue-removing catheter as set forth in claim 1, wherein the adjustment mechanism comprises a spool having an axis of rotation oriented transverse to the longitudinal axis of the catheter body.

6. A tissue-removing catheter as set forth in claim 5, wherein the proximal end portions of the first and second adjustment lines are operatively attached to the spool.

7. A tissue-removing catheter as set forth in claim 6, wherein the spool is configured to be selectively rotated about the axis of rotation in a first rotational direction to simultaneously decrease said effective length of the first adjustment line and increase said effective length of the second adjustment line.

8. A tissue-removing catheter as set forth in claim 7, wherein the spool is further configured to be selectively rotated about the axis of rotation in a second rotational direction, opposite the first rotational direction, to simultaneously increase said effective length of the first adjustment line and decrease said effective length of the second adjustment line.

9. A tissue-removing catheter as set forth in claim 1, wherein the first and second adjustment lines are disposed diametrically opposite one another relative to the longitudinal axis.

10. A tissue-removing catheter as set forth in claim 1, wherein the first and second adjustment lines comprise respective first and second wires.

11. A tissue-removing catheter as set forth in claim 10, wherein the first and second wires are generally non-elastic.

12. A tissue-removing catheter as set forth in claim 1, wherein the adjustment mechanism is operable to configure the distal end portion of the catheter body from a straight configuration to a bent configuration, and from the bent configuration to the straight configuration.

13. A tissue-removing catheter as set forth in claim 12, wherein the effective lengths of the first and second adjustment lines are generally equal when the distal end portion of the catheter body is in the straight configuration.

14. A tissue-removing catheter as set forth in claim 12, wherein the adjustment mechanism and the first and second adjustment lines are configured to resist bending of the distal end portion of the catheter body when the distal end portion is in the straight configuration.

15. A tissue-removing catheter as set forth in claim 1, wherein the first and second connection points are proximal the tissue-removing element.

16. A tissue-removing catheter as set forth in claim 15, wherein the catheter body includes a rigid collar located at the first and second connection points, the distal end portions of the first and second adjustment lines being fastened to the rigid collar.

17. A tissue-removing catheter as set forth in claim 1, wherein the jacket has a first shore hardness at the bending longitudinal portion and a second shore hardness at the proximally-adjacent longitudinal portion, the first shore hardness being less than the second shore hardness.

18. A tissue-removing catheter as set forth in claim 1, wherein the catheter body further includes a braided reinforcement received in the jacket and extending circumferentially around the drive shaft.

19. A tissue-removing catheter as set forth in claim 18, wherein the braided reinforcement has a first pick rate at the bending longitudinal portion and a second pick rate at the proximally-adjacent longitudinal portion, the first pick rate being less than the second pick rate.

20. A tissue-removing catheter as set forth in claim 1, wherein the support coil has a first radial thickness at the bending longitudinal portion and a second radial thickness at the proximally-adjacent longitudinal portion, the first radial thickness being smaller than the second radial thickness.

21. A tissue-removing catheter as set forth in claim 1, further comprising a sleeve received in the jacket in radially spaced apart relationship with the longitudinal axis of the catheter body, one of the first and second adjustment lines being received in the sleeve for movement relative to the catheter body along the longitudinal axis.

22. A tissue-removing catheter comprising:
an elongate catheter body configured for insertion into a body lumen of a subject, the catheter body having a proximal end portion, an opposite distal end portion, and a longitudinal axis extending between the distal and proximal end portions;
a tissue-removing element located adjacent the distal end portion of the catheter body configured to remove tissue from the body lumen;
first and second adjustment lines extending along the catheter body at circumferentially spaced apart locations about the longitudinal axis, the first and second adjustment lines having distal end portions attached to the catheter body at respective first and second connection points adjacent the distal end portion of the catheter body, and the first and second adjustment lines having opposite proximal end portions; and
an adjustment mechanism operatively connected to the proximal end portions of the first and second adjustment lines, wherein the adjustment mechanism is selectively operable to decrease an effective length of the first adjustment line extending between the first connection point and the adjustment mechanism to bend the distal end portion of the catheter body in a first direction and urge the tissue-removing element in the first direction, wherein the adjustment mechanism is selectively operable to decrease an effective length of the second adjustment line extending between the second connection point and the adjustment mechanism to bend the distal end portion of the catheter body in a second direction different than the first direction and urge the tissue-removing element in the second direction;
wherein the distal end portion includes a bending longitudinal portion and a proximally-adjacent longitudinal portion that is immediately proximal to the bending longitudinal portion;
wherein the catheter body includes a drive shaft extending along the longitudinal axis and a jacket extending circumferentially around the drive shaft;
wherein the catheter body further includes a braided reinforcement received in the jacket and extending circumferentially around the drive shaft; and
wherein the braided reinforcement is stiffer along the proximally-adjacent longitudinal portion than along the bending longitudinal portion such that the bending longitudinal portion of the catheter body has a bending stiffness that is less than a bending stiffness of the proximally-adjacent longitudinal portion of the catheter body.

* * * * *